US006934585B1

(12) United States Patent
Schloss et al.

(10) Patent No.: US 6,934,585 B1
(45) Date of Patent: Aug. 23, 2005

(54) SYSTEM AND METHOD FOR FAR-FIELD R-WAVE DETECTION

(75) Inventors: Harold C. Schloss, Los Angeles, CA (US); Junyu Mai, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 462 days.

(21) Appl. No.: 10/176,554

(22) Filed: Jun. 21, 2002

(51) Int. Cl.[7] ............................................. A61N 1/362
(52) U.S. Cl. ........................................................ 607/9
(58) Field of Search ...................................... 607/4–30

(56) References Cited

U.S. PATENT DOCUMENTS

| 4,515,161 A | * | 5/1985 | Wittkampf et al. ........... 607/27 |
| 5,247,929 A | * | 9/1993 | Stoop et al. .................. 607/14 |
| 5,658,320 A | | 8/1997 | Betzold et al. ............... 607/14 |
| 5,759,196 A | | 6/1998 | Hess et al. .................... 607/14 |
| 5,814,083 A | | 9/1998 | Hess et al. .................... 607/14 |

FOREIGN PATENT DOCUMENTS

WO  WO 97/11745  4/1997  .......... A61N 1/362

* cited by examiner

*Primary Examiner*—Scott M. Getzow

(57) ABSTRACT

A system and corresponding method are disclosed for discriminating between far field R-waves and actual atrial events that are sensed on an atrial sense channel. In one embodiment, such information is used to prevent mode switching. In another embodiment, the information is used to extend an atrial blanking period so that the far field R-waves are no longer sensed on an atrial channel.

46 Claims, 5 Drawing Sheets

SYSTEM AND METHOD FOR FAR-FIELD R-WAVE DETECTION

FIELD OF THE INVENTION

The present invention generally relates to implantable cardiac stimulation devices and, more particularly, to systems and methods associated therewith that are capable of discriminating between far-field R-waves and atrial events.

BACKGROUND

Patients with heart problems are often treated by surgical implantation of a cardiac stimulation device (such as an implantable cardioverter-defibrillator, or "ICD") providing one or more stimulation therapies, such as pacing, cardioversion or defibrillation. Many ICDs provide "dual chamber" therapy—that is, the ICD is capable of sensing activity in an atrium and in a ventricle, and is also capable of delivering stimulation energy to the atrium and/or the ventricle.

ICDs are capable of operating in various modes. One such mode is a DDD mode, in which the ICD senses activity in both the right atrium and right ventricle, and also is capable of delivering stimulation energy to both the right atrium and right ventricle.

In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber.

ICDs operating in a DDD mode generally function as follows. If an intrinsic atrial depolarization signal (a P-wave) is not detected by the atrial channel before an escape interval times out, a stimulating pulse will be delivered to depolarize the atrium to cause atrial contraction. Following either a detected P-wave or an atrial pacing pulse, the ventricular channel attempts to detect a depolarization signal in the ventricle, known as an R-wave. If no R-wave is detected within a defined atrial-ventricular interval (AV interval, also referred to as AV delay), a stimulation pulse is delivered to the ventricle to cause ventricular depolarization. In this way, rhythmic dual chamber pacing is achieved by coordinating the delivery of ventricular output in response to a sensed or paced atrial event.

ICDs are also capable of switching modes, for example, from DDD to VVI, in which the ICD no longer uses atrial activity to control ventricular activity. One scenario in which the device would switch from DDD to VVI is when an atrial tachyarrhythmia is occurring. In DDD mode, the atrial tachyarrhythmia could cause a ventricular tachyarrhythmia to occur (referred to as pacemaker mediated tachycardia (PMT)). Therefore, upon detection of atrial tachyarrhythmia, many ICDs switch modes to VVI or some other mode in which the atrial activity is not used to control the ventricular activity. Many other mode switches are also well known to those skilled in the art, including switching to an antitachycardia pacing mode.

In some instances, devices switch modes due to false indicators of atrial tachyarrhythmias. One such false indicator is far field R-waves, namely ventricular depolarizations that are sensed by atrial sensing circuitry and erroneously believed to be atrial depolarizations. When far-field R-waves are counted as atrial events along with actual atrial events, the ICD will determine that the atrial rate is higher than it actually is, which may cause the ICD to incorrectly believe that an atrial tachyarrhythmia is occurring and to inappropriately switch modes.

It would therefore be advantageous to provide an implantable cardiac stimulation device capable of discriminating between actual atrial events and far-field R-waves.

SUMMARY

What is disclosed herein is a system and corresponding method for discriminating between far field R-waves and actual atrial events that are sensed on an atrial sense channel. In one embodiment, such information is used to prevent mode switching. In another embodiment, the information is used to extend an atrial blanking period so that the far field R-waves are no longer sensed on an atrial channel.

In one embodiment, a method is disclosed in which ventricular events and subsequent atrial events are detected. Interval values are then computed for multiple pairs of ventricular and atrial events. Those interval values are then processed to determine if those values are substantially constant. If so, then far-field sensing is determined to exist.

In another illustrative embodiment, diagnostic information is generated and can be transmitted to an external device for display and/or further processing. Preferably, the diagnostic information can be in the form of a histogram of interval values.

Other and further features, advantages, and benefits of the invention will become apparent in the following description taken in conjunction with the following drawings. It is to be understood that the foregoing general description and the following detailed description are exemplary and explanatory but are not to be restrictive. The accompanying drawings which are incorporated in and constitute a part of this invention, illustrate one of the embodiments of the invention, and together with the description, serve to explain the principles of the invention in general terms. Like numerals refer to like parts throughout the disclosure.

DETAILED DESCRIPTION OF THE PREFERRED EMBODIMENTS

Figure 1:
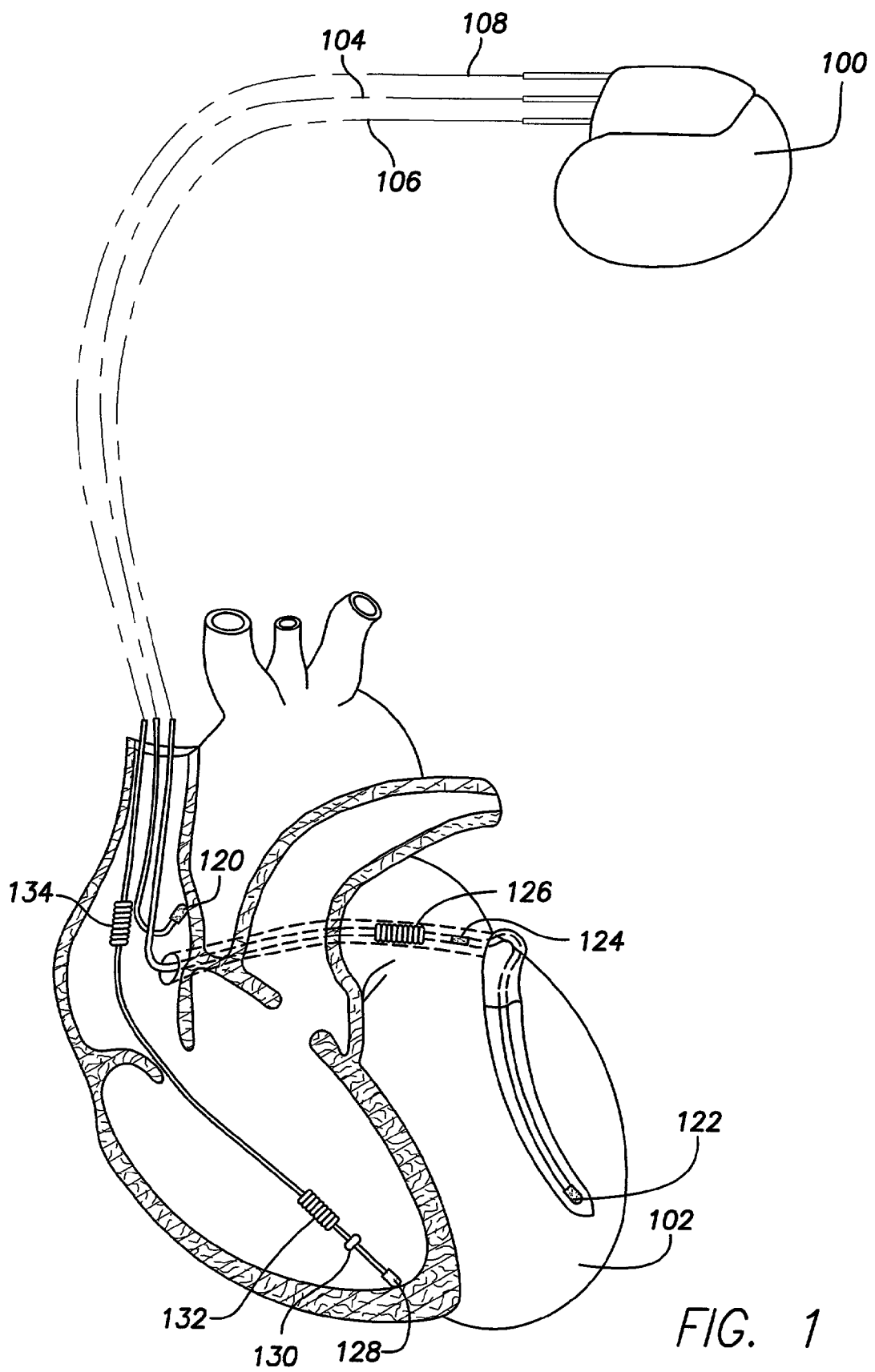
FIG. 1 is a diagram illustrating a cardiac stimulation device in communication with a patient's heart.

FIG. 1 is a simplified diagram illustrating an implantable cardiac stimulation device 100 (as may be utilized in connection with one or more embodiments disclosed herein) in communication with a patient's heart 102. In the particular example illustrated in FIG. 1, the implantable cardiac stimulation device 100 is electrically connected to the patient's heart 102 by way of three leads 104, 106, and 108, suitable for multi-chamber sensing and delivery of stimulating pulses and/or shock therapy. Generally, the implantable cardiac stimulation device 100 senses cardiac activity in, and delivers stimulating pulses or electrical shocks to, the atria and ventricles of the patient's heart 102 via leads 104, 106, and 108.

To sense atrial cardiac signals and to provide right atrial chamber stimulation therapy, stimulation device 100 is preferably coupled to an implantable right atrial lead 104 having at least an atrial tip electrode 120, which typically is implanted in the patient's right atrial appendage. To sense left atrial and ventricular cardiac signals and to provide left chamber pacing therapy, stimulation device 100 is preferably coupled to a coronary sinus lead 106 designed for placement in the coronary sinus region via the coronary sinus by positioning a distal electrode adjacent to the left ventricle and/or additional electrode(s) adjacent to the left atrium. The coronary sinus region in the present context generally refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. A preferred coronary sinus lead 106 is configured to receive atrial and ventricular cardiac signals, and to deliver left ventricular pacing therapy using a left ventricular tip electrode 122, left atrial pacing therapy using a left atrial ring electrode 124, and shocking therapy using a left atrial coil electrode 126. In each case, the electrical return path may be a different lead or the housing of the cardiac stimulation device 100 itself, according to the particular design employed.

The implantable cardiac stimulation device 100 is preferably also in electrical communication with the patient's heart 102 by way of an implantable right ventricular lead 108 having, in the exemplary implementation illustrated in FIG. 1, a right ventricular tip electrode 128, a right ventricular ring electrode/sensor 130, a right ventricular (RV) coil electrode 132, and a superior vena cava (SVC) coil electrode 134. In typical implantations, the right ventricular lead 108 is transvenously inserted into the heart 102 in such a manner that the right ventricular tip electrode 128 is positioned in the right ventricular apex, the RV coil electrode 132 is positioned in the right ventricle, and the SVC coil electrode 134 is positioned in the superior vena cava. The right ventricular lead 108 is thereby capable of receiving cardiac signals, and delivering stimulation in the form of pacing and/or shock therapy, to the right ventricle.

Figure 2:
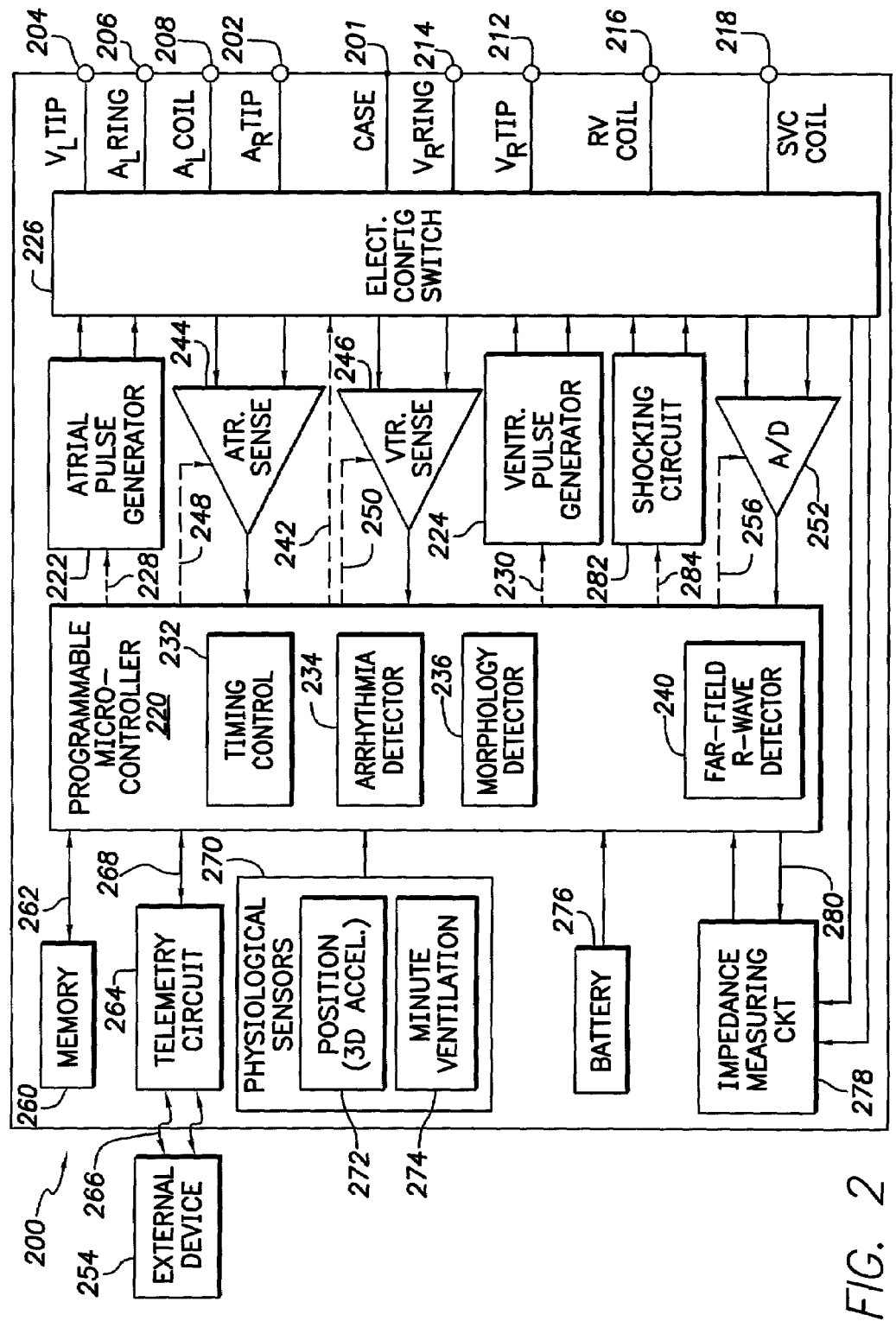
FIG. 2 is a simplified, functional block diagram depicting various components of an exemplary cardiac stimulation device according to one embodiment as disclosed herein.

FIG. 2 is a simplified, functional block diagram depicting various components of an exemplary cardiac stimulation device system 200, as may be incorporated (in whole or part) into an implantable cardiac stimulation device such as, for example, cardiac stimulation device 100 illustrated in FIG. 1. Preferably, the cardiac stimulation device system 200 is capable of providing cardioversion, defibrillation, and pacing stimulation therapies in as many as all four chambers of the patient's heart for treating fast or slow arrhythmias, or other heart conditions, although in some cases a more streamlined set of functional features will be desired. Likewise, the principles as have been and will be described herein are not only applicable to multi-chamber devices, but also to single-chamber, devices. It will be understood and appreciated by those skilled in the art that various components or features in the FIG. 2 system 200 could be duplicated, eliminated, or disabled, in various combinations, while still operating according to the principles as described herein.

As illustrated in FIG. 2, among the electrical connections provided in the cardiac stimulation device system 200 is a case "electrode" connection 201 to the housing of the cardiac stimulation device. The housing for an implantable cardiac stimulation device is often referred to as the "can," "case" or "case electrode," and the case electrode connection 201 may in some cases be selected, via appropriate programming parameters, to act as the return electrode for various "unipolar" modes. The housing, through the case electrode connection 201, may further be used as a return electrode for shocking purposes, either alone or in combination with one or more coil electrodes (such as coil electrodes 126, 132 and 134 illustrated in FIG. 1). Further illustrated, from a schematic standpoint, are signal terminals 202, 204, 206, 208, 212, 214, 216 and 218 (the names of the electrodes or other component to which the terminals are intended to be attached are shown next to each terminal). Preferably, the housing of the cardiac stimulation device includes a connector (not shown) providing a means for connecting the terminals 202, 204, 206, 208, 212, 214, 216, and 218 to their respective electrodes or other components.

For right atrial sensing and pacing, the connector preferably includes a right atrial tip terminal (AR TIP) 202 adapted for connection to the atrial tip electrode 120. For left chamber sensing, pacing, and shocking, the connector preferably includes a left ventricular tip terminal ($V_L$ TIP) 204, a left atrial ring terminal ($A_L$ RING) 206, and a left atrial shocking terminal ($A_L$ COIL) 208, which are adapted for connection to the left ventricular ring electrode 122, the left atrial tip electrode 124, and the left atrial coil electrode 126, respectively.

For right chamber sensing, pacing, and shocking, the connector further preferably includes a right ventricular tip terminal ($V_R$ TIP) 212, a right ventricular ring terminal ($V_R$ RING) 214, a right ventricular shocking terminal ($R_V$ COIL) 216, and an SVC shocking terminal (SVC COIL) 218, which are adapted for connection to the right ventricular tip electrode 128, right ventricular ring electrode 130, the RV coil electrode 132, and the SVC coil electrode 134, respectively.

A programmable microcontroller 220 is preferably provided in the cardiac device stimulation system 200 to, among other things, control the various modes of stimulation therapy. As is well known in the art, microcontroller 220 typically includes a microprocessor, or equivalent control circuitry, designed specifically for controlling the delivery of stimulation therapy, and may further include volatile (e.g., RAM) and/or non-volatile (e.g., ROM) memory, logic and timing circuitry, state machine circuitry, and I/O circuitry. Typically, microcontroller 220 includes the ability to process or monitor input signals (data) as controlled by a program code stored in a designated block of memory. The specific type of microcontroller 220 is not critical to the described implementations. Rather, any suitable microcontroller 220 may be used that is capable of carrying out the functions described herein. The use of microprocessor-based control circuits for performing timing and data analysis functions are well known in the art.

FIG. 2 further shows, in connection with the cardiac device stimulation system 200, an atrial pulse generator 222 and a ventricular pulse generator 224 for generating pacing stimulation pulses to be delivered by the right atrial lead 104, the coronary sinus lead 106, and/or the right ventricular lead 108, preferably via an electrode configuration switch 226. To provide stimulation therapy in each of the four chambers of the heart, the atrial and ventricular pulse generators 222, 224 may include dedicated, independent pulse generators, multiplexed pulse generators, or shared pulse generators. In the example shown in FIG. 2, the pulse generators 222, 224 are controlled by the microcontroller 220 through control signals 228 and 230, respectively, which serve the purpose of triggering or inhibiting the stimulation pulses.

The microcontroller 220 may include, in the form of, e.g., digital circuitry, microcode or program instructions, or a combination thereof, various functional blocks which facilitate control of the various aspects of the cardiac stimulation device system 200. For example, the microcontroller 220 may include timing control circuitry 232 to control the timing of the stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc. These types of timing functions are well known in the art.

Microcontroller 220 further may include one or more of an arrhythmia detector 234, a morphology detector 236, and a far field R-wave detector 240. These components can be utilized by the cardiac stimulation device system 200 to detect and treat various cardiac conditions requiring treatment. The arrhythmia detector 234, morphology detector 236, and far field R-wave detector 240 may be implemented, e.g., in hardware as part of the microcontroller 220, or as software/firmware instructions programmed into the device and executed on the microcontroller 220 during certain modes of operation.

In the example illustrated in FIG. 2, the electronic configuration switch 226 preferably comprises a plurality of internal switches (not shown) for connecting the desired terminals (e.g., terminals 202, 204, 206, etc.) to the appropriate input/output circuits, thereby providing complete electrode programmability. The electronic configuration switch 226, in response to a control signal 242 from the microcontroller 220, determines the polarity of the stimulation pulses (e.g., unipolar, bipolar, combipolar, etc.) by selectively opening/closing the appropriate combination of internal switches, in a manner well known in the art.

To sense activity in any or all chambers of the heart, atrial sensing circuit 244 and ventricular sensing circuit 246 may be selectively coupled to the right atrial lead 104, coronary sinus lead 106, and the right ventricular lead 108, preferably through the electronic configuration switch 226. The atrial sensing circuit 244 and ventricular sensing circuit 246 may include, e.g., dedicated sense amplifiers, multiplexed amplifiers, or shared amplifiers. The electronic configuration switch 226 preferably determines the "sensing polarity" of the cardiac signal by selectively opening/closing the appropriate internal switches, in a manner well understood in the art. The foregoing features allow the clinician to program the sensing polarity independent of the stimulation polarity.

Each sensing circuit 244 and 246 preferably employs one or more low power, precision amplifiers with programmable gain and/or automatic gain control, bandpass filtering, and threshold detection circuitry, as known in the art, to selectively sense the cardiac signal of interest. The automatic gain control assists the cardiac stimulation device system 200 with sensing the typically low amplitude signal characteristics associated with atrial or ventricular fibrillation.

The outputs of the atrial and ventricular sensing circuits 244 and 246 are connected to the microcontroller 220 which, in turn, is able to trigger or inhibit the atrial and ventricular pulse generators 222 and 224, respectively, in a programmable fashion in response to the absence or presence of cardiac activity in the appropriate chambers of the heart. The sensing circuits 244 and 246, in turn, receive control signals over signal lines 248 and 250 from the microcontroller 220 for purposes of controlling the gain or threshold of the sensing circuits 244, 246, any polarization charge removal circuitry (not shown), and/or the timing of any blocking circuitry (not shown) coupled to the inputs of the sensing circuits 244, 246, all in a manner well understood in the art.

For arrhythmia detection, the cardiac stimulation device system 200 may utilize the atrial and ventricular sensing circuits 244, 246 to sense cardiac signals, which can be analyzed to determine whether a particular cardiac rhythm is physiologic or pathologic. Generally, as used herein, the term "sensing" refers to the noting of an electrical signal, while the term "detection" refers to the processing of sensed signals and noting the presence of an arrhythmia or other specific cardiac event or activity. The timing intervals between sensed events (e.g., P-waves, R-waves, and T-waves) are preferably classified by the arrhythmia detector 234 of the microcontroller 220 by, e.g., comparing the intervals to predefined rate zone limits (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (preferably including bradycardia pacing, anti-tachycardia pacing, or cardioversion/defibrillation shocks, all three of which are collectively referred to as "tiered therapy", as well as mode switching). The algorithm described herein may be used in conjunction with the arrhythmia detector 234 to prevent improper mode switches, as is described in detail below.

Cardiac signals may, in addition to being applied to atrial and ventricular sensing circuits 244, 246, also be applied to inputs of an analog-to-digital (A/D) data acquisition system 252. The A/D data acquisition system 252 is preferably configured to acquire intracardiac electrogram signals, convert the raw analog data into a digital signal, and store the digital data for later processing and/or telemetric transmission to an external device 254. The data acquisition system 252 may be selectively coupled to the right atrial lead 104, the coronary sinus lead 106, and the right ventricular lead 108 through the electronic configuration switch 226 to allow sampling of cardiac signals across any desired pair of electrodes.

Advantageously, the data acquisition system 252 may be coupled to the microcontroller 220, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 220 generally detects a depolarization signal during a window following a stimulation pulse, the presence of which indicates that capture has occurred. The microcontroller 220 enables capture detection by triggering the ventricular pulse generator 224 to generate a stimulation pulse, starting a capture detection window using the timing control circuitry 232 within the microcontroller 220, and enabling the data acquisition system 252 via control signal 256 to sample the cardiac signal that falls in the capture detection window and, based on the amplitude, determine if capture has occurred.

Capture detection may occur on a beat-by-beat basis or on a sampled basis. A capture threshold search can desirably be performed at regular intervals—e.g., once a day during at least the acute phase (e.g., the first 30 days after implantation) and less frequently thereafter. A capture threshold search procedure begins at a desired starting point (e.g., a high energy level, or else the level at which capture is currently occurring) and decreases the energy level until capture is lost. The value at which capture is lost is known as the capture threshold. Thereafter, a safety margin may be added to the capture threshold to arrive at a pacing stimulus energy value.

The microcontroller 220 is generally coupled, via a data/address bus 262, to a memory 260, wherein the programmable operating parameters used by the microcontroller 220 are stored and modified, as required, in order to customize the operation of the stimulation device 100 to suit the needs of a particular patient. Such operating parameters may define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. The memory 260 is preferably large enough to store a relatively large amount of data (e.g., from the data acquisition system 252), which may be read out at a later time (by telemetry) and used for subsequent analysis to guide the programming of the device.

Advantageously, the operating parameters of the implantable device 100 may be non-invasively programmed into the memory 260 through a telemetry circuit 264 in telemetric communication via communication link 266 with an external device 254, such as a programmer, transtelephonic transceiver, or a diagnostic system analyzer. The microcontroller 220 activates the telemetry circuit 264 with a control signal 268. The telemetry circuit 264 may allow intracardiac electrograms (ECGs) and status information relating to the operation of the device 100 (as contained in the microcontroller 220 or memory 260) to be sent to the external device 254 through an established communication link 266.

The cardiac stimulation device system 200 can further include one or more physiologic sensors 270, such as a "rate-responsive" sensor which is used to adjust pacing stimulation rate according to the activity level of the patient. The physiological sensor 270 may alternatively, or in addition, be used to detect changes in cardiac output, changes in the physiological condition of the heart, or diurnal changes in activity (e.g., detecting sleep and wake states). The microcontroller 220 may be programmed to respond to information received from the physiologic sensor 270 by, e.g., adjusting the various pacing parameters (such as rate, AV Delay, V—V Delay, etc.) at which the atrial and ventricular pulse generators 222, 224, generate stimulation pulses, or by making other dynamic adjustments. While shown in FIG. 2 as being included within the stimulation device, the physiologic sensor 270 may instead be external to the stimulation device, yet still be implanted within or carried by the patient. Examples of physiologic sensors that may be implemented in cardiac stimulation device system 200 include sensors that, for example, sense respiration rate and/or minute ventilation, pH of blood, ventricular gradient, and so forth. The physiological sensor 270 may also be embodied, for example, with reference to FIG. 1, as a pressure sensor that is coupled to detect RV pressure that is sensed by a sensor located at ring 130, which can perform dual functions of a ring electrode and a pressure sensor.

The one or more physiological sensors 270 may further include one or more sensors for detecting position or postural changes. Any sensor capable of sensing such changes, either directly or indirectly, may be used for such a purpose. In particular, the one or more physiological sensors 270 may include an activity or position sensor (not shown) mounted within the housing of the stimulation device to detect movement in the patient's position. The activity or position sensor may be implemented in many ways, including as a 3D accelerometer, a sensor that detects the earth's magnetic or gravitational fields, a MEMs (micro-electro mechanical) device, and the like. Another sensor that may be used is of the type that detects activity variance.

The cardiac stimulation device system 200 additionally includes a battery 276 for providing operating power to the circuitry shown in FIG. 2. For an implantable cardiac device employing cardioversion or defibrillation shock therapy, the battery 276 is preferably capable of operating at low current drains (preferably less than, e.g., 10 $\mu$A) for long periods of time, and of providing high-current pulses (for capacitor charging) when the patient requires a shock pulse. The battery 276 also desirably has a predictable discharge characteristic so that elective replacement time can be detected. As one example, the battery 276 may be of the lithium/silver vanadium oxide variety.

The cardiac stimulation device system 200 can further include magnet detection circuitry (not shown), coupled to the microcontroller 220, to detect when a magnet is placed in near proximity to the cardiac stimulation device. A magnet may be used, for example, by a clinician to perform various test functions of the cardiac stimulation device and/or to signal the microcontroller 220 that the external programmer 254 is in place to exchange data with the microcontroller 220 through the telemetry circuits 264.

The cardiac stimulation device system 200 further may include an impedance measuring circuit 278, enabled by the microcontroller 220 via a control signal 280. Examples of uses for an impedance measuring circuit 278 include, among other things, (1) lead impedance surveillance during the acute and chronic phases for proper lead positioning or dislodgment; (2) electrode operability verification (and automatic switching to an operable pair if dislodgment occurs); (3) measurement of respiration or minute ventilation; (4) measurement of thoracic impedance for determining shock thresholds; (5) detection of whether the device has been implanted; (6) measurement of stroke volume; and (7) detection of the opening of heart valves. The impedance measuring circuit 278 is advantageously coupled to the electronic configuration switch 226 so that any desired electrode may be used in connection with the impedance measuring circuit 278.

Microcontroller 220 also controls a shocking circuit 282 through a control signal 284 (or set of control signals). The shocking circuit 282 may be programmed to generate shock pulses of different selectable energy magnitudes—for example, of low (up to 0.5 joules), moderate (0.5–10 joules), or high energy (11 to 40 joules)—as controlled by the microcontroller 220. Such shock pulses are ordinarily applied to the patient's heart through at least two shocking electrodes, which, referring now to FIG. 1, may be selected from the left atrial coil electrode 126, the RV coil electrode 132, and/or the SVC coil electrode 134. The housing of the cardiac stimulation device may act as an active electrode in combination with the RV electrode 132, or as part of a split electrical vector using the SVC coil electrode 134 or the left atrial coil electrode 126 (i.e., using the RV electrode as a common electrode).

Cardioversion shocks tend to be of low to moderate energy level (so as to minimize pain felt by the patient), and may be synchronized with an R-wave. Cardioversion therapy tends to be utilized, generally, for the treatment of tachycardia. Defibrillation shocks are generally of moderate to high energy level (e.g., in the range of 5–40 joules), delivered synchronously or asynchronously (since R-waves may be too disorganized during a fibrillation episode).

Defibrillation shocks are generally utilized for treating fibrillation. The microcontroller 220 is preferably capable of controlling the synchronous or asynchronous delivery of the shock pulses, and the provision of synchronous or asynchronous shocks may be either programmable (and may further be tailored to the particular mode or degree of therapy) or may be set by default in whole or part.

According to a preferred embodiment, cardiac stimulation device 100 is configured to monitor ventricular-to-atrial intervals (V-A intervals) for a plurality of pairs of events (where each pair consists of a ventricular event and the subsequent atrial event). The intervals are processed to determine if those intervals are substantially constant or stable. If they are, then it is determined that the atrial "events" are in fact far field R-waves. A generalized flow diagram of a preferred method for far field R-wave discrimination is illustrated in FIG. 3.

Figure 3:
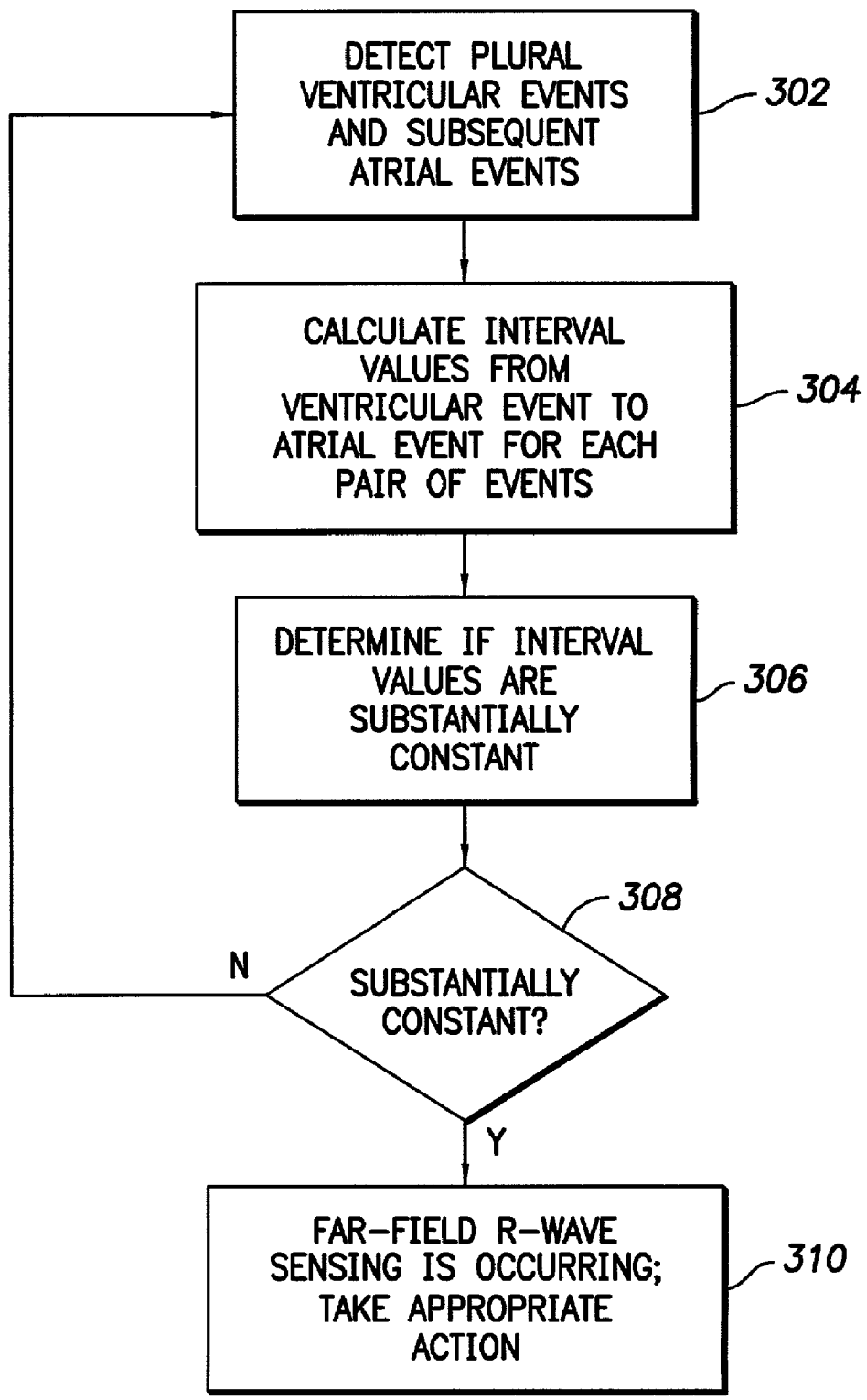
FIG. 3 is a flow chart depicting an illustrative method for detecting far field R-waves.

As shown in FIG. 3, in a first step 302 the far-field R-wave discrimination process is started. In step 302, a plurality of ventricular events and subsequent atrial events are detected.

At step 304, for each pair of events (i.e., a ventricular event and the subsequent atrial event) an interval value is calculated. In one embodiment, interval values for the last four pairs of events are calculated, although it will be apparent to those skilled in the art that more or less than four pairs of events may be used. Preferably, the interval values are all recently obtained values, for example, those obtained within the last ten seconds. In another embodiment, each interval value calculated at step 304 is processed to provide diagnostic information to a physician, as is described in more detail below.

In one illustrative embodiment, only those pairs of events (ventricular event followed by an atrial event) that are followed by another atrial event prior to a detected ventricular event are used by the algorithm. Those pairs of events that satisfy that requirement are likely to result from either far-field R-wave sensing or an atrial tachyarrhythmia, whereas those pairs of events that do not satisfy that requirement are likely to result from actual atrial events. Atrial tachyarrhythmias will have very unstable interval values and therefore are easily distinguished from far-field R-wave sensing.

At step 306, those interval values are processed to determine if the interval values are substantially constant. It will be apparent that many different methods may be utilized to determine if the interval values are substantially constant. Examples of such methods are described below.

At query block 308, the algorithm determines whether the interval values are substantially constant. If not, then operation returns to step 302, and the atrial events are not considered to be far-field R-waves. In that event, the device's arrhythmia detector 234 may determine that an atrial arrhythmia exists, which will cause device 100 to take appropriate measures, such as switching modes and the like.

If at query block 308 the process determines that the interval values are substantially constant, then operation proceeds to step 310, and the sensed atrial events are determined to be far-field R-waves rather than actual atrial depolarizations. At step 310, the algorithm then takes appropriate action, which can take many different forms. In one embodiment, the atrial blanking period may be extended so that the far-field R-waves are no longer sensed by the atrial sensing channel. In another embodiment, the device may prevent an automatic mode switch from taking place, since it has been determined that the premature atrial events are not actual atrial depolarizations. In yet another embodiment, a record of the result can be made, such as by setting a flag or storing the record in memory, for subsequent transmission during interrogation by an external programmer. In still another embodiment, the device may prevent a defibrillation shock from being applied to the atrium.

In one embodiment, the atrial events must occur within a specified detection window in order to be used by the far-field R-wave detection algorithm. Atrial events falling outside the detection window are ignored for purposes of the algorithm. In one embodiment, the detection window is defined as the period from the end of the PVAB (post-ventricular atrial blanking period) to the end of the PVARP (post-ventricular atrial refractory period). In other embodiments, other detection windows may be used. For example, a patient-specific detection window may be defined, or any other suitable detection window as will be readily understood by those skilled in the art.

In another embodiment, in addition to determining whether the interval values are substantially constant, the algorithm also determines whether the interval values are relatively short. For example, this may be accomplished by determining whether the average interval value is below a preset threshold value, such as about 250 milliseconds.

Figure 5:
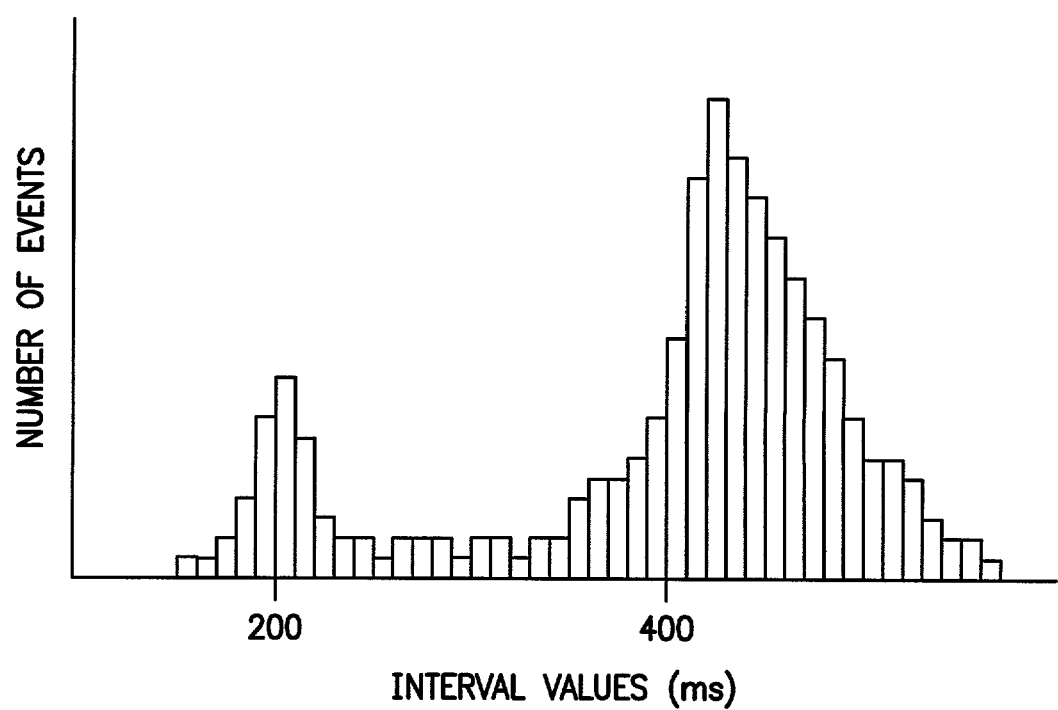
FIG. 5 is a histogram generated by the device of FIG. 1 in accordance with one illustrative embodiment.

As described above, in one alternative embodiment, the algorithm processes the interval values to provide diagnostic information, which in one embodiment may be in the form of a histogram (FIG. 5). As is shown in FIG. 5, the majority of the interval values are due to sinus rhythm (actual atrial depolarizations) and would be relatively long values (e.g., greater than 400 milliseconds). If the device experiences far-field sensing, then the histogram displays an additional cluster of interval values that would have a very small range of values, for example on the order of about 200 millseconds.

In one illustrative embodiment, as described above, only those pairs of events that are followed by another atrial event are used in constructing the histogram. In that case, the stability of the interval values determines whether far-field R-wave sensing is occurring. In yet another embodiment, only those interval values below a preset value (e.g., 400 milliseconds) are used to construct the histogram. Again, the stability of the interval values would indicate whether far-field R-wave sensing is occurring, as opposed to an arrhythmia, premature atrial contractions, and the like, which would result in relatively unstable interval values.

In another embodiment, the diagnostic information could simply be statistical information, such as an average interval value and a standard deviation for the interval values. It will be apparent to those skilled in the art that the diagnostic information can take many different forms, such as a percentage of events, when those events happened, a counter of such events, and the like. Such information may be stored in an event record, such as the one described in U.S. Pat. No. 5,487,755 to Snell et al., which is expressly incorporated herein by reference.

Figure 4:
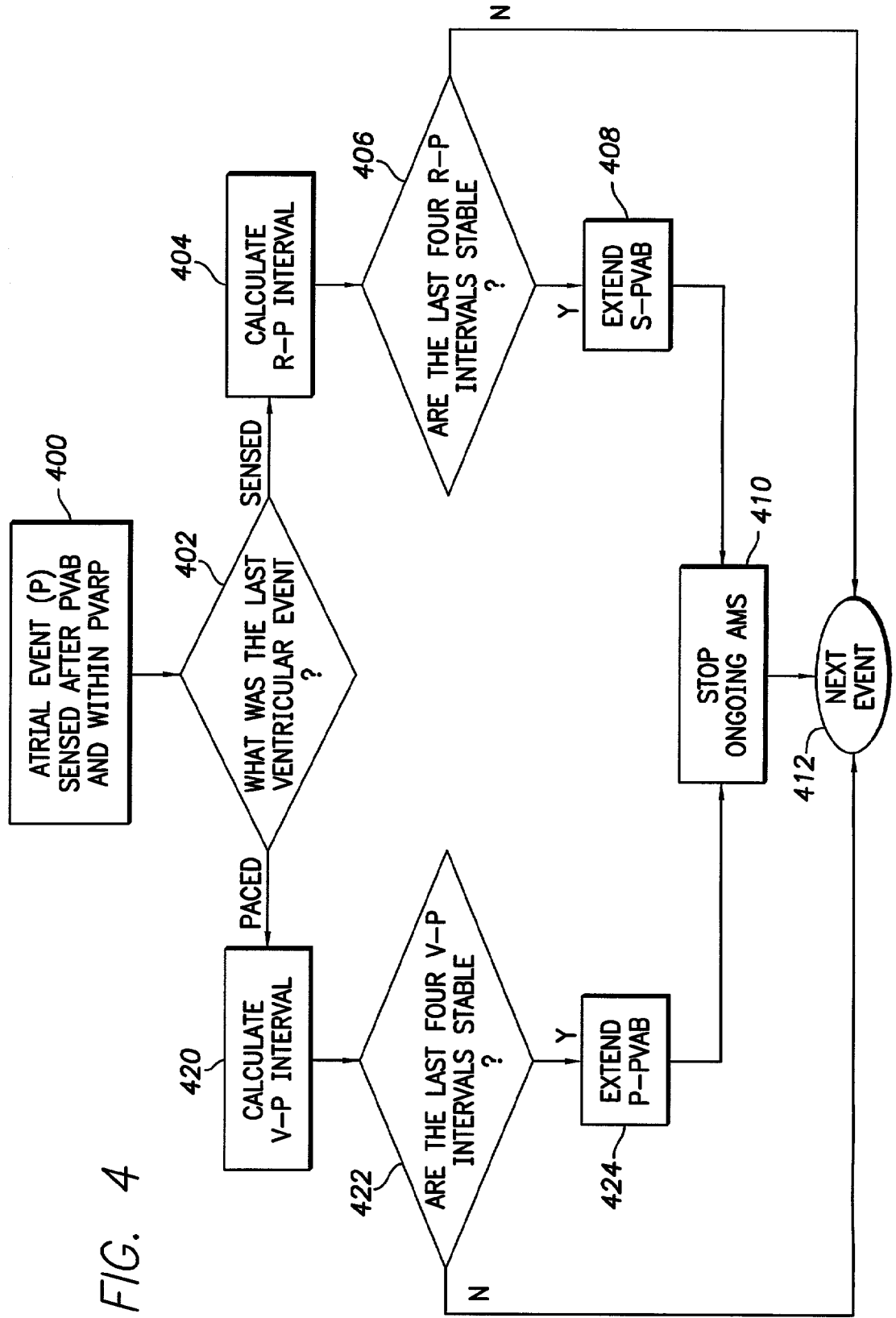
FIG. 4 is a flow chart depicting another illustrative method for detecting far-field R-waves.

Referring now to FIG. 4, there is shown a flowchart of another illustrative embodiment. In this embodiment, two different groups of interval values are computed, one for paced ventricular events and the other for sensed ventricular events. In addition, two different PVAB values are maintained, one for use after paced ventricular events and the other for use after sensed ventricular events.

According to this embodiment, operation commences at step 400 with an atrial event being sensed within a detection window that extends from the end of PVAB to the end of PVARP.

Once an atrial event is detected within the detection window, operation proceeds to query block 402, where the algorithm determines the type of ventricular event that preceded the atrial event, namely whether the preceding ventricular event was a paced event (as determined by monitoring for applied ventricular pacing pulses) or a sensed (intrinsic) event (as determined by sensing a ventricular depolarization). If the preceding ventricular event was a sensed event, then operation proceeds to step 404, and an interval value is calculated from the occurrence of the intrinsic event (R-wave) to the occurrence of the subsequent atrial event (hereinafter referred to as an "R-P interval"). Operation then proceeds to block 406, and the last four R-P interval values are processed to determine if those R-P interval values are substantially constant. If not, then operation proceeds to step 412. If on the other hand the R-P interval values are substantially constant, then operation proceeds to step 408, and a PVAB value for sensed ventricular events (S-PVAB) is increased by an amount. As described above, the algorithm may use more or less than four interval values. In addition, the R-P interval values are preferably obtained within the last ten seconds (or some other similar period of time).

Operation proceeds from step 408 to step 410, where the algorithm stops any ongoing automatic mode switch that may be taking place. Operation then proceeds to step 412 to await the next cardiac event, at which time operation returns to step 400.

If at query block 402 the preceding ventricular event was a paced event, operation instead proceeds to step 420, and an interval value is determined from the paced ventricular event (V-pace) to the sensed atrial event (hereinafter referred to as the "V-P interval").

Then, at block 422, the last four of the V-P interval values (preferably obtained within the last ten seconds) are processed to determine if those V-P interval values are substantially constant. If not, then operation proceeds to step 412. If on the other hand the V-P interval values are substantially constant, then operation proceeds to step 424, and a PVAB value for paced ventricular events (V-PVAB) is increased by an amount. Operation then proceeds to step 410, as described above.

It will be understood that the extended V-PVAB will be used for future paced ventricular events, while the extended S-PVAB will be used for future sensed ventricular events. In this embodiment, two different PVAB values are used because the duration of ventricular events can vary depending on whether the ventricular event is an intrinsic or a paced event.

In one embodiment, the stability of the interval values is determined by calculating an averaged deviation for the interval values, and by then comparing the averaged deviation with a threshold value. The averaged deviation is based on the following equation (for V-P interval values):

$$\text{Averaged deviation} = \Sigma |V\text{-}P(1{:}4) - \text{mean } (V\text{-}P(1{:}4))|/4$$

For example, if the four V-P interval values are 10, 14, 16, and 20 msec, then the mean V-P interval value is 15 msec, and the averaged deviation is 3 msec.

In one embodiment, the threshold value is on the order of 20 msec, although other threshold values may also be used. Thus, if the averaged deviation is less than 20 msec, then the interval values are determined to be stable (i.e., far-field R-wave sensing is occurring). A similar equation is used for the R-P interval values. Other methods may be used to determine the stability of the interval values, including determining whether all of the interval values are within some predefined value of each other, and the like.

In one illustrative embodiment, one or more of the above-described embodiments are always in use by device 100 to monitor for far-field R-wave sensing. In another embodiment, device 100 is programmed to retrieve and execute the far-field R-wave algorithm only during periods of increased patient activity, such as during exercise, because the R-wave amplitude or duration might change during exercise, such that in some patients far-field R-waves may be detected only during exercise. In one embodiment, the algorithm is only executed when the patient's atrial rate gradually increases in a manner indicative of exercise. Alternately, the algorithm may be executed when the one or more physiologic sensors 270 indicate periods of increased activity.

While preferred embodiments have been described herein, many variations are possible which remain within the concept and scope of the invention. Such variations would become clear to one of ordinary skill in the art after inspection of the specification and the drawings. The invention therefore is not to be restricted except within the spirit and scope of any appended claims.

What is claimed is:

1. In an implantable cardiac stimulation device, a method comprising:
    sensing a plurality of ventricular events and atrial events;
    calculating a plurality of ventricular-to-atrial interval values based on the sensed ventricular and atrial events;
    processing the interval values to determine if the interval values are substantially constant; and
    initiating a predetermined action if the interval values are substantially constant;
    wherein initiating a predetermined action comprises preventing mode switching.

2. In an implantable cardiac stimulation device, a method comprising:
    sensing a plurality of ventricular events and atrial events;
    calculating a plurality of ventricular-to-atrial interval values based on the sensed ventricular and atrial events;
    processing the interval values to determine if the interval values are substantially constant;
    initiating a predetermined action if the interval values are substantially constant; and
    determining if the patient is at an increased activity level, and performing the acts of sensing, calculating, processing, and initiating only if the patient is at an increased activity level.

3. The method of claim 2, wherein sensing ventricular events comprises sensing intrinsic ventricular events.

4. The method of claim 2, wherein sensing ventricular events comprises monitoring for ventricular pacing pulses.

5. The method of claim 2, wherein processing the interval values comprises calculating an averaged deviation value based on the plurality of interval values.

6. The method of claim 2, wherein sensing atrial events comprises defining a detection window based on a sensed ventricular event, and monitoring for an atrial event occurring within the detection window.

7. The method of claim 2, wherein calculating interval values comprises calculating interval values for at least four pairs of ventricular and atrial events.

8. The method of claim 2, wherein initiating a predetermined action comprises extending an atrial blanking period.

9. The method of claim 2, wherein calculating interval values comprises calculating interval values for all pairs of ventricular and atrial events occurring within a predetermined duration.

10. The method of claim 2, further comprising storing the interval values as diagnostic data, and transmitting the diagnostic data to an external device.

11. The method of claim 2, wherein processing comprises calculating an averaged deviation for the interval values, and comparing the averaged deviation with a threshold value.

12. The method of claim 11, wherein the threshold value is on the order of approximately 20 milliseconds.

13. In an implantable cardiac stimulation device, a method comprising:
    sensing a plurality of ventricular events and subsequent atrial events;
    calculating interval values between the ventricular events and subsequent atrial events for a plurality of pairs of events;
    processing the interval values to determine if the interval values are substantially constant;
    extending an atrial blanking period if the interval values are substantially constant; and
    stopping an ongoing mode switch if the interval values are substantially constant.

14. The method of claim 13, wherein sensing ventricular events comprises sensing intrinsic ventricular events.

15. The method of claim 13, wherein extending an atrial blanking period comprises extending an atrial blanking period following intrinsic ventricular events.

16. The method of claim 13, wherein sensing ventricular events comprises monitoring for ventricular pacing pulses.

17. The method of claim 16, wherein extending an atrial blanking period comprises extending an atrial blanking period following ventricular pacing pulses.

18. The method of claim 13, wherein processing the interval values comprises calculating an averaged deviation value based on the plurality of interval values, and comparing the averaged deviation with a predetermined threshold value.

19. The method of claim 18, wherein the threshold value is on the order of approximately 20 milliseconds.

20. The method of claim 13, wherein sensing subsequent atrial events comprises defining a detection window based on a sensed ventricular event, and monitoring for an atrial event occurring within the detection window.

21. The method of claim 13, wherein calculating interval values comprises calculating interval values for at least four pairs of ventricular and atrial events.

22. The method of claim 13, wherein calculating interval values comprises calculating interval values for all pairs of ventricular and atrial events occurring within a predetermined duration of time.

23. The method of claim 22, wherein calculating interval values comprises calculating interval values for all pairs of ventricular and atrial events occurring within a period of about ten seconds.

24. In an implantable cardiac stimulation device, a method comprising:
    sensing a plurality of ventricular events and subsequent atrial events;
    calculating interval values between the ventricular events and subsequent atrial events for a plurality of pairs of events;
    processing the interval values to determine if the interval values are substantially constant; and
    extending an atrial blanking period if the interval values are substantially constant; and
    determining if the patient is at an increased activity level, and performing the acts of sensing, calculating, processing, and extending only if the patient is at an increased activity level.

25. In an implantable cardiac stimulation device, a method comprising:
    sensing a plurality of ventricular events and subsequent atrial events;
    calculating interval values between the ventricular events and subsequent atrial events for a plurality of pairs of events;
    processing the interval values to determine if the interval values are substantially constant; and
    preventing mode switching if the interval values are substantially constant.

26. The method of claim 25, wherein sensing ventricular events comprises sensing intrinsic ventricular events.

27. The method of claim 25, further comprising extending an atrial blanking period if the interval values are substantially constant.

28. The method of claim 25, wherein sensing ventricular events comprises sensing paced ventricular events.

29. The method of claim 25, wherein processing the interval values comprises calculating an averaged deviation value based on the plurality of interval values, and comparing the averaged deviation value with a predetermined threshold value.

30. The method of claim 29, wherein the threshold value is on the order of approximately 20 milliseconds.

31. The method of claim 25, further comprising determining if the patient is at an increased activity level, and performing the acts of sensing, calculating, processing, and preventing only if the patient is at an increased activity level.

32. The method of claim 25, wherein sensing subsequent atrial events comprises defining a detection window based on a sensed ventricular event, and monitoring for an atrial event occurring within the detection window.

33. The method of claim 25, wherein calculating interval values comprises calculating interval values for at least four pairs of ventricular and atrial events.

34. The method of claim 25, wherein calculating interval values comprises calculating interval values for all pairs of ventricular and atrial events occurring within a predetermined duration.

35. The method of claim 34, wherein calculating interval values comprises calculating interval values for all pairs of ventricular and atrial events occurring within a period of about ten seconds.

36. An implantable cardiac stimulation device comprising:
    sensing circuitry that is operative to sense a plurality of ventricular events and subsequent atrial events; and
    control circuitry that is operative to calculate interval values, between a ventricular event and a subsequent atrial event, for a plurality of pairs of events, to compare the plurality of interval values to determine if the interval values are substantially stable, and to take predetermined action if a stable interval exists;
    wherein the control circuitry is operative to determine if the patient is at an increased activity level, and is responsive to the patient not being at the increased activity level to ignore the interval values.

37. The device of claim 36, wherein the sensing circuitry is operative to sense intrinsic ventricular events.

38. The device of claim 36, wherein the control circuitry is operative to calculate an averaged deviation value based on the plurality of interval values, and to compare the averaged deviation value with a predetermined threshold value.

39. The device of claim 38, wherein the threshold value is on the order of approximately 20 milliseconds.

40. The device of claim 36, wherein the control circuitry is operative to define a detection window based on a sensed ventricular event, and monitor for an atrial event occurring within the detection window.

41. The device of claim 36, wherein the control circuitry is operative to calculate interval values for at least four pairs of ventricular and atrial events.

42. The device of claim 36, wherein the control circuitry is operative to extend an atrial blanking period if far-field sensing exists.

43. The device of claim 36, wherein the control circuitry is operative to calculate interval values for all pairs of ventricular and atrial events occurring within a predetermined duration.

44. The device of claim 36, wherein the control circuitry is further operative to generate diagnostic data from the sensed events, and further comprising telemetry circuitry that is operative to transmit the diagnostic data to an external device.

45. An implantable cardiac stimulation device comprising:
sensing circuitry that is operative to sense a plurality of ventricular events and subsequent atrial events; and
control circuitry that is operative to calculate interval values, between a ventricular event and a subsequent atrial event, for a plurality of pairs of events, to compare the plurality of interval values to determine if the interval values are substantially stable, and to take predetermined action if a stable interval exists;
wherein the control circuitry is operative to prevent mode switching if far-field sensing exists.

46. An implantable cardiac device comprising:
means for sensing ventricular and atrial events;
means for calculating a plurality of ventricular-to-atrial interval values;
means for ignoring the interval values if the patient is not at an increased activity level;
means for determining if the interval values are substantially constant; and
means for initiating a predetermined action if the interval values are substantially constant.

* * * * *